(12) United States Patent
Trueba (10) Patent No.: US 11,259,827 B2
(45) Date of Patent: Mar. 1, 2022

(54) CORING TOOL

(71) Applicant: HeartWare, Inc., Miami Lakes, FL (US)

(72) Inventor: William Trueba, Miami, FL (US)

(73) Assignee: HeartWare, Inc., Miami Lakes, FL (US)

( * ) Notice: Subject to any disclaimer, the term of this patent is extended or adjusted under 35 U.S.C. 154(b) by 285 days.

(21) Appl. No.: 16/161,675

(22) Filed: Oct. 16, 2018

(65) Prior Publication Data
US 2019/0046221 A1 Feb. 14, 2019

Related U.S. Application Data

(62) Division of application No. 13/974,920, filed on Aug. 23, 2013, now Pat. No. 10,117,663.
(Continued)

(51) Int. Cl.
*A61B 17/32* (2006.01)
*A61B 17/3205* (2006.01)
(Continued)

(52) U.S. Cl.
CPC ........ *A61B 17/32* (2013.01); *A61B 17/32053* (2013.01); *A61B 17/3417* (2013.01);
(Continued)

(58) Field of Classification Search
CPC .............. A61B 17/32; A61B 17/32053; A61B 17/3417; A61B 2017/2912; A61B 2017/2923; A61B 17/3425
See application file for complete search history.

(56) References Cited

U.S. PATENT DOCUMENTS 5,980,545 A 11/1999 Pacala et al.
6,080,173 A 6/2000 Williamson, IV et al.
(Continued)

FOREIGN PATENT DOCUMENTS

WO 2011123446 A1 10/2011
WO 2012092932 A1 7/2012

OTHER PUBLICATIONS

Extended European Search Report for Application No. EP13830516 dated Feb. 15, 2016.
(Continued)

*Primary Examiner* — Tan-Uyen T Ho
*Assistant Examiner* — Rachel S Highland
(74) *Attorney, Agent, or Firm* — Shumaker & Sieffert, P.A.

(57) ABSTRACT

The present invention related to a coring tool for preparing a core or opening through tissue and methods of use thereof. In one embodiment, the present invention include a coring tool including: (a) a frame having proximal and distal directions; (b) an operator interface element mounted to the frame and movable between a rest position and an actuated position; (c) a coring head having at least one cutting blade, the coring head being mounted to the frame for movement in the proximal and distal directions; and (d) a actuation mechanism connected between the coring head and the operator interface element, the actuation mechanism including a selector element having first and second positions, the actuation mechanism being arranged to move the coring head distally responsive to movement of the interface element from the rest position toward the actuated position when the selector element is in the first position, and to move the coring head proximally responsive to movement of the interface element from the rest position toward the actuated position when the selector element is in the second position.

6 Claims, 4 Drawing Sheets

Related U.S. Application Data

(60) Provisional application No. 61/692,477, filed on Aug. 23, 2012.

(51) Int. Cl.
　　*A61B 17/34*　　　(2006.01)
　　*A61B 17/00*　　　(2006.01)
　　*A61B 17/29*　　　(2006.01)
　　*A61M 60/00*　　　(2021.01)
　　*A61M 60/122*　　 (2021.01)
　　*A61M 60/857*　　 (2021.01)

(52) U.S. Cl.
　　CPC ............... *A61B 2017/00252* (2013.01); *A61B 2017/2912* (2013.01); *A61B 2017/2923* (2013.01); *A61B 2017/3425* (2013.01); *A61M 60/00* (2021.01); *A61M 60/122* (2021.01); *A61M 60/857* (2021.01)

(56) References Cited

U.S. PATENT DOCUMENTS

| | | |
|---|---|---|
| 9,949,817 B2 | 4/2018 | Wesselmann et al. |
| 2004/0171905 A1 | 9/2004 | Yu et al. |
| 2005/0251187 A1 | 11/2005 | Beane et al. |
| 2007/0134993 A1 | 6/2007 | Tamez et al. |
| 2009/0012552 A1 | 1/2009 | Pandey et al. |
| 2012/0010455 A1 | 1/2012 | Reichenbach et al. |

OTHER PUBLICATIONS

International Search Report for Application No. PCT/US2013/056451 dated Feb. 7, 2014.

CORING TOOL

CROSS-REFERENCE TO RELATED APPLICATIONS

This application is a divisional of U.S. patent application Ser. No. 13/974,920, filed Aug. 23, 2013, which application is related to and claims priority from U.S. Provisional Patent Application Ser. No. 61/692,477, filed Aug. 23, 2012, the entirety of all of which are incorporated herein by reference.

BACKGROUND OF THE INVENTION

The present invention relates to instruments and methods used in connection with preparation of tissue of a patient, particularly the tissue of the heart of a mammalian subject. In a particular instance, the instruments and methods of the present invention are used in preparing the heart for implantation of a ventricular assist device.

In certain disease states, the heart lacks sufficient pumping capacity to meet the needs of the body. This inadequacy can be alleviated by providing a mechanical pump referred to herein as a heart pump or a ventricular assist device ("VAD") to supplement the pumping action of the heart.

Figure 3A:
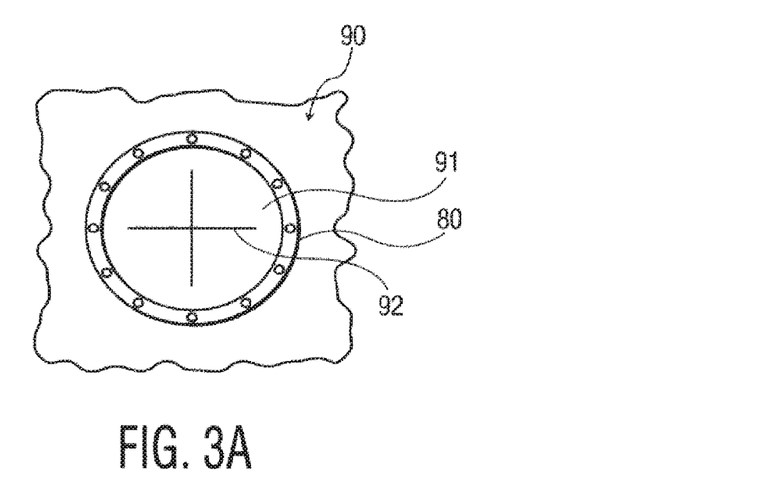
FIG. 3A illustrates an example of a sewing ring secured to a heart wall.

The VAD is typically connected to the heart by an inflow tube, most commonly to the left ventricle. Typically, one end of an outflow tube is connected to the VAD and the other end is connected to the aorta. Once connected, the VAD and the heart both pump blood from the left ventricle to the ascending or descending aorta to improve blood flow. Alternatively, a VAD may be connected to the ventricle to assist the heart in pumping blood into pulmonary arteries. In some instances, the VAD is connected to the heart through the use of a sewing ring, as disclosed in U.S. Published Patent Application Nos. 2004/0171905 and 2007/0134993, the disclosures of which are both hereby incorporated by reference herein as if fully set forth herein. An example of the sewing ring is illustrated in FIG. 3A. A separate surgical tool is then used to cut or core a hole in the ventricle centered within the sewing ring. The VAD is typically attached to the sewing ring at the site of the cored hole in the ventricle. Alternatively, the VAD can be secured to the sewing ring such that the VAD is positioned through the heart wall and thus a portion of the VAD is within the heart and a portion is outside the heart.

As used currently, the step of coring the tissue within the sewing ring can be difficult to perform. Typically, the surgeon must advance the coring tool and then retract it. This requires two separate and opposite motions. Moreover, if the coring tool is movably mounted in a housing so that the surgeon can aim the coring tool by aiming the housing, the surgeon must advance the coring tool relative to the housing and then retract the coring tool relative to the housing, all while attempting to maintain the housing in position relative to the patient.

Thus, there is a need for an improved coring tool that is simple to actuate and perform the tissue coring, and further allows the operator to maintain affirmative pressure against the heart wall and/or sewing ring during such actuation.

BRIEF SUMMARY OF THE INVENTION

In one embodiment, the present invention Includes a coring tool including a proximal handle, a distal coring head and a shaft extending therebetween. The shaft can include an actuation rod extending from the distal coring head to the handle. The proximal handle includes an operator interface element and an actuation mechanism which connects the operator interface element to the rod, and thus, the distal coring head. In one example, the actuation mechanism can include a first actuator and a second actuator.

In another embodiment, the present invention includes a coring tool including a frame having proximal and distal directions; an operator interface element mounted to the frame and movable between a rest position and an actuated position; a coring head having at least one cutting blade, the coring head being mounted to the frame for movement in the proximal and distal directions; and a actuation mechanism connected between the coring head and the operator interface element, the actuation mechanism including a selector element having first and second positions, the actuation mechanism being arranged to move the coring head distally responsive to movement of the interface element from the rest position toward the actuated position when the selector element is in the first position, and to move the coring head proximally responsive to movement of the interface element from the rest position toward the actuated position when the selector element is in the second position.

Further, the frame can include a shaft having proximal and distal ends and a handle extending transverse to the shaft adjacent the proximal end of the shaft, and wherein the operator interface element is mounted to the frame for movement generally towards and away from the handle, the operator interface element being remote from the handle in the rest position and adjacent the handle in the actuated position. Further, the tool can include an actuation mechanism wherein the mechanism may be arranged so that movement of the operator interface element from the actuated position to the rest position does not move the coring head.

In a further embodiment, the present invention includes a coring tool having a frame having proximal and distal directions; a proximal handle including an operator interface element and an actuation mechanism including a first actuator and a second actuator and a selector mechanism connected to both the first and second actuators; a distal coring head including at least one cutting blade mounted to the frame, the at least one blade actuatable between a first position and a second position by the actuation mechanism; and a shaft extending between the handle and the distal coring head including an actuation rod extending from the distal coring head to the actuation mechanism. The operator interface element may be biased in the rest position.

Further, the first position of the distal coring head may be a closed position wherein the blade is positioned adjacent to a distal end of the shaft, and the second position of the distal coring head may be an open position wherein the blade is spaced from the distal end of the shaft, the blade in the second position is adapted to form a cored opening in tissue. The operator interface element can actuate the distal coring head between the first position and the second position via the actuation mechanism. Moreover, the selector mechanism may selectably engage one of the first actuator or the second actuator to both the operator interface element and the actuation rod.

In still another embodiment, the present invention includes a method of actuating a distal coring head of a coring tool, including the steps of applying a force to an operator interface element of the coring tool, the operator interface element biased in a rest position opposite the direction of application of the force such that the force moves the operator interface element to an actuated position, the application of force moving the distal coring head from a first position to a second position; removing the force from the operator interface element to allow the operator interface element to return to the rest position while the distal coring head remains in the second position; toggling a selector mechanism affiliated with the operator interface element; applying the force to the operator interface element a second time to move the distal coring head from the second position to the first position; and removing the force from the operator interface element while the distal coring head remains in the first position, thereby allowing the operator interface element to return to the rest position. Further, the operator interface element can be a biased trigger, and the step of applying the force may include gripping the trigger and applying a squeezing force to the trigger to move the trigger from the rest position, spaced from a handle of the coring tool, to the actuated position positioned relatively closer to the handle.

In yet a further embodiment, the present invention includes a method of coring tissue including the steps of positioning a coring tool adjacent the tissue; manually moving an operator interface element of the coring tool relative to a frame of the coring tool from a rest position toward an actuated position so as to advance a coring head in a distal direction relative to the frame causing the coring head to advance into the tissue; then returning the operator interface element toward the rest position while leaving a coring head in position relative to the frame; and then manually moving the operator interface element of the coring tool toward the actuated position again so as to retract the coring head in the proximal direction relative the frame and thus retract the coring head relative to the tissue.

In one example of this embodiment, the steps of moving the operator interface element toward the actuated position can include squeezing the operator interface element toward a handle incorporated in the frame. Further, the manually moving steps can be performed using one hand, and wherein the same hand may be used to grasp the handle and maintain the frame of the coring tool in position relative to the tissue. Additionally, the step of maintaining the frame in position relative to the tissue may include maintaining the frame in engagement with a sewing ring attached to the tissue. In a further example, the tissue can be a wall of a heart in a mammalian subject.

Additionally, this embodiment can further include the step of moving a selector element of a mechanism from a first position to a second position between the "manually moving" steps. In another alternative, the coring head can have a blade facing in the proximal direction so that the coring head cuts a core from the tissue during the step of manually moving the operator interface element toward the actuated position a second time.

In another embodiment, the present invention includes a method of forming a cored opening in tissue, comprising the steps of accessing the tissue with a distal coring head of a coring tool, the coring tool also including a proximal handle including an operator interface element biased on one direction and an actuation mechanism including a first actuator and a second actuator and a selector mechanism connected to both the first and second actuators, the distal coring head including at least one cutting blade, the at least one blade actuatable between a first position and a second position by the actuation mechanism, and a shaft extending between the handle and the distal coring head including an actuation rod extending from the distal coring head to the actuation mechanism; upon accessing the tissue, applying a force to the operator interface element to move the distal coring head from the first position to the second position via the first actuator and actuation rod, wherein the first position of the distal coring head is a closed position in that the blade is positioned adjacent to a distal end of the shaft, and the second position of the distal coring head is an open position in that the blade is spaced from the distal end of the shaft; releasing the operator interface element while the distal coring head remains in the second position and engaging the selector mechanism to engage the second actuator; applying the force to the actuator a second time to move the distal coring head from the second position to the first position, wherein as the distal coring head moves to the first position, the distal coring head traps the cored tissue within a volume of the distal coring head; and removing the coring tool and the cored tissue from the adjacent tissue. For example, the selector mechanism is a toggle switch, wherein the engaging step includes toggling the toggle switch between engagement of either the first actuator or the second actuator to the actuation rod. Also, the operator interface element can be a trigger, and the step of applying the force includes gripping the trigger and applying a squeezing force to the trigger.

BRIEF DESCRIPTION OF THE DRAWINGS

FIGS. 4A and 48 illustrate an alternative embodiment of the distal coring head.

DETAILED DESCRIPTION

The coring tool of the present invention is intended for use in the preparation of tissue in a patient. Specifically, the coring tool is used to form a cored opening in the tissue for the passage of implants, additional tools, or the like. More particularly, the coring tool is used to form a cored opening through heart wall tissue in a mammalian subject or patient and into a ventricle of the heart, specifically the left ventricle, within the perimeter of a sewing ring secured to the heart wall tissue, such that a VAD can be positioned and secured therethrough. While this particular method of use will form the focus of the disclosure herein, it is envisioned that the coring tool may be used on other tissues, with or without a sewing ring present, and for other procedures than the placement of a VAD. As used herein, "proximal" or "proximally" means closer to or towards the operator, e.g., surgeon, while "distal" or "distally" means further from or away from the operator.

Figure 1:
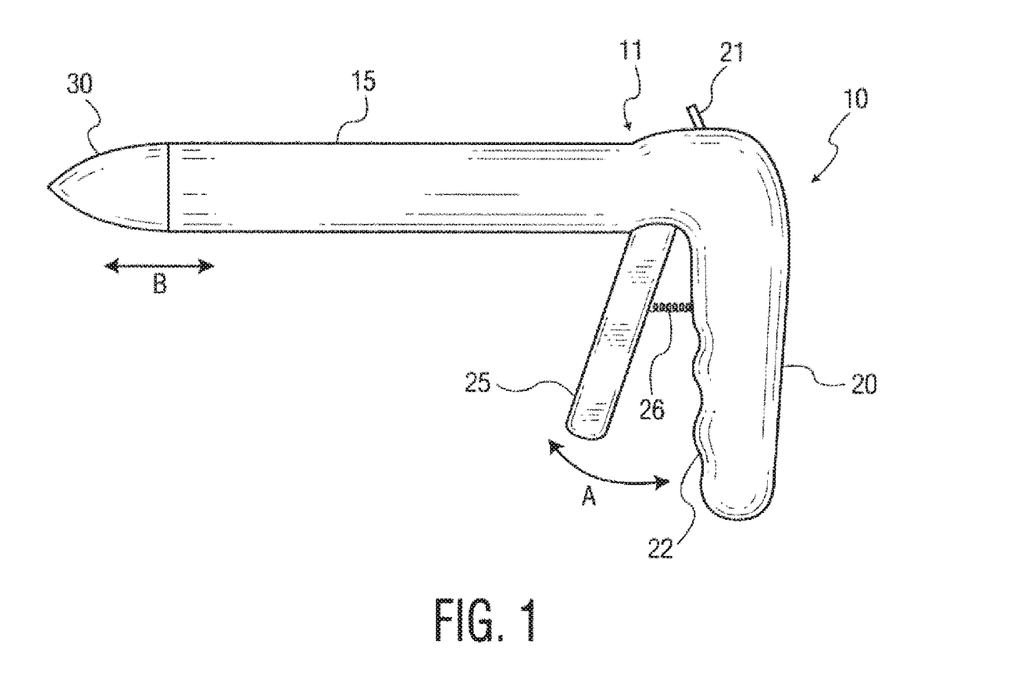
FIG. 1 illustrates one embodiment of the coring tool of the present invention.
Figure 1A:
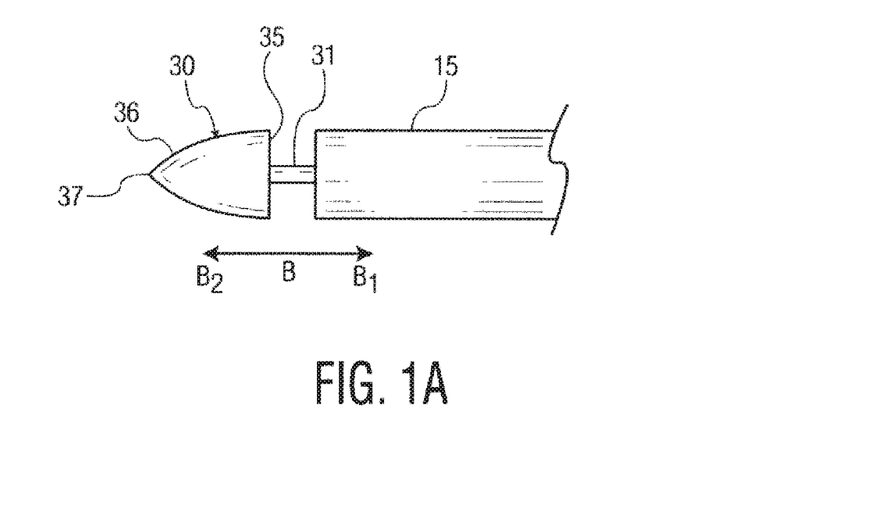
FIG. 1A illustrates one embodiment of the actuation of a distal coring tip of the coring tool of FIG. 1.

In one embodiment, as illustrated in FIG. 1, a coring tool 10 includes a frame 11 incorporating a handle 20 and a hollow shaft 15 extending in the distal direction from the handle. A distal coring head 30 is disposed distal to shaft 15. As illustrated in FIG. 1A, the distal coring head can include at least one blade 35 on a proximal surface of the coring head 30. The coring head also can include a tapered outer surface 36 extending to a distal-most point 37, or similar shape, suitable to provide for simplified access through tissue. Such a distal coring head is similar to that included on the Apical Coring Tool (HeartWare, Inc., Miami Lakes, Fla.), commercialized by the assignee of the present application. The coring head is actuatable, via an actuation rod 31 extending through the shaft 15, in the direction "B" between a proximal, first position $B_1$ and a distal, second position $B_2$, as explained in greater detail below. In the proximal, first position, the distal coring head is in a closed position in which the blade is positioned adjacent to the distal end of the shaft 15. In the distal second position, the distal coring head is in an open position such that the blade 35 is spaced from the distal end of the shaft.

Returning to FIG. 1, opposite the distal coring head 30, and integrated with shaft 15, is the handle 20. The handle includes a handle grip 22 which can be ergonomically shaped for steady and comfortable gripping by a hand of the operator. An operator interface element 25, such as a trigger (as illustrated) or the like, is mounted to the frame 11 adjacent handle 20. The operator interface element is movable in a direction relative to the frame between a rest position illustrated in solid lines in FIG. 2, and an actuated position depicted in broken lines (as handle 25'). In the depicted embodiment of FIG. 1, the operator interface element 25 is mounted for pivoting motion relative to the frame 11 as indicated by arrow "A" between the rest position and the actuated position. In the rest position, the operator interface element 25 is remote from the handle 20, whereas in the actuated position the operator interface element 25 is adjacent handle 20. As illustrated, for example, the operator interface 25 is biased toward the rest position by a biasing mechanism, such as spring 26.

Figure 2:
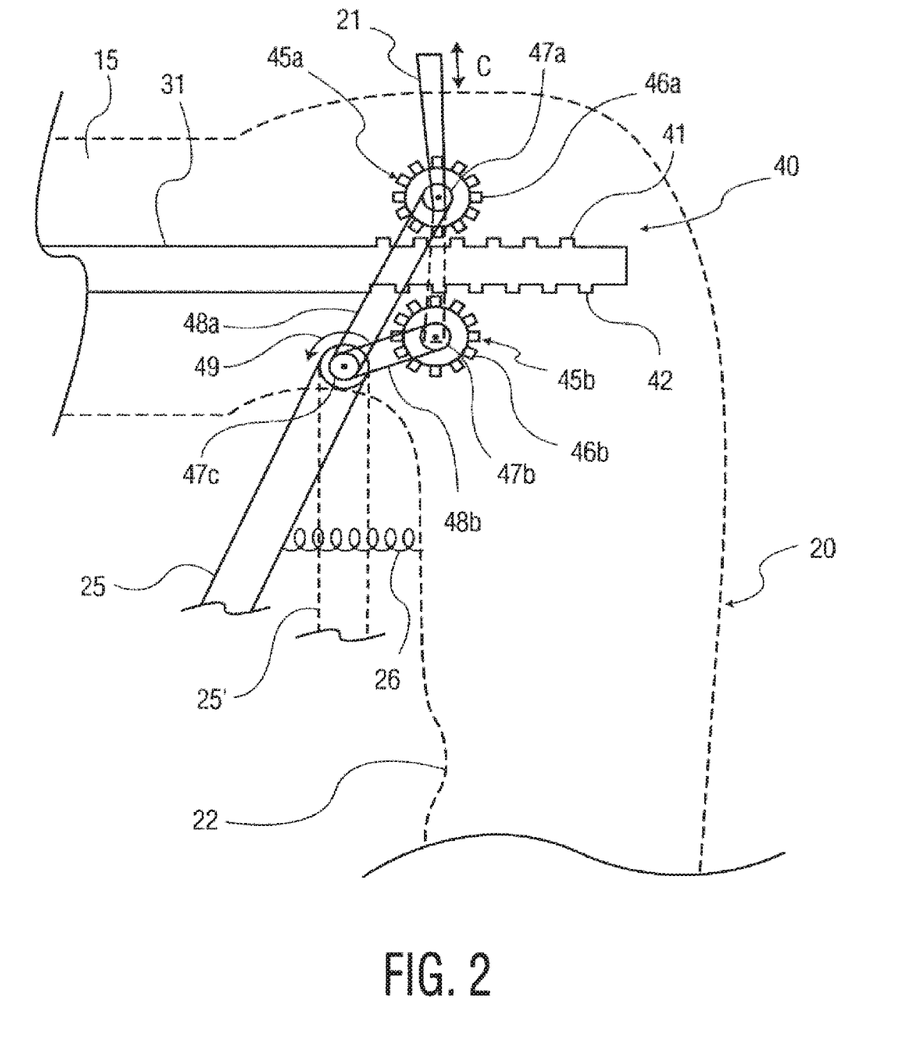
FIG. 2 illustrates one embodiment of a handle of the coring tool of FIG. 1.

An actuation mechanism 40 (FIG. 2) is mounted to frame 11. The actuation mechanism can include a selector mechanism 21 which can be, for example, a toggle switch, button, or the like. FIG. 2 illustrates one embodiment of the actuation mechanism 40 positioned within frame 11. In this embodiment, the actuation mechanism includes a first actuator 45a and a second actuator 45b, both of which are connected to the selector mechanism 21. Both the first and second actuators are also connected to the operator interface element 25 via a pulley system 47a, 47b, 47c and 48a, 48b, 48c, though other connections are also possible. In one variation, pulley 47c can be connected to operator interface element 25 through a unidirectional connection such as a ratchet clutch schematically indicated at line 49 so that pulley 47c will be driven in rotation upon movement of element 25 from its rest position to its actuated position, but will not be driven upon return movement of element 25 from the actuated position to the rest position.

Continuing with this exemplary embodiment, an example of a method of operation of this coring tool 10 is described. As illustrated in FIG. 2, either one of the first and second actuators 45a, 45b can interact with a proximal end of the actuation rod 31 to move the actuation rod, and thus, the distal coring tip between the first position $B_1$ and second position $B_2$. The interaction between the first and second actuators and the actuation rod can be through a rack and pinion system, as illustrated, such that a plurality of teeth 46a, 46b on either of the first and second actuators can interdigitate and engage a matching track of teeth 41, 42 on the distal end of the alignment rod 31. Thus, for example, the selector mechanism 21, illustrated as a toggle button movable in the direction "C", may selectably engage one of the first or second actuators with the actuation rod. Upon applying a force to the operator interface element, the selected actuator engages the actuation rod and moves it in a pre-determined direction dependent upon the actuator 45a, 45b selected. As illustrated, if the first actuator 45a is selected, upon movement of the operator interface element 25 from its rest position to its actuated position, the first actuator will move the actuating rod 31 in the proximal direction, such that the distal coring head 30 would move towards the first position $B_1$. Conversely, if the second actuator 45b is selected, upon movement of the operator interface element 25 from its rest position to its actuated position, the actuator 45b would move the actuation rod 31 distally, and thus would actuate the distal coring head to the second position $B_2$.

Furthermore, upon removal of the force on the operator interface 25, and return movement of the operator interface element 25 to its rest position, the selected actuator 45a, 45b, the actuation rod 31, and the distal coring head 30 remain in substantially the same position.

In another embodiment, the present invention includes a method of actuating a distal coring head 30 of a coring tool 10. Once again using the exemplary actuation mechanism 40 of FIG. 2, the method includes first confirming that the selector mechanism 21 is toggled such that the (for example) second actuator 45b engages the actuation rod 31. Next, the operator applies a force to the operator interface element 25 in a direction opposite the direction in which the interface element is biased—i.e., proximally towards the grip 22. The force moves the interface element 25 from its rest position to its actuated position. Such motion actuates the actuation rod 31 via the second actuator 45b, which moves the distal coring head 30 from the first position $B_1$ to the second position $B_2$. Once the coring head is in the second position, the force is removed from the operator interface element 25 and the interface element returns to its rest position, but the coring head remains in the second position.

Then, the selector mechanism is toggled such that the second actuator 45b is disengaged from the actuation rod 31 and the first actuator 45a is engaged with the actuation rod. Next, the force is once again applied to the operator interface element 25, which moves the interface element from its rest position to its actuated position, and actuates the actuation rod via the first actuator, which returns the distal coring head 30 back to the first position $B_1$ from the second position $B_2$. The force is once again removed from the interface element and the interface element returns to its biased position, but the coring head remains in the first position.

The coring tool 10 of the present invention is used, in one embodiment, to form a core or cut in tissue, and in one specific application, in heart wall tissue of a mammalian patient. For example, the coring tool may form a core or opening in the wall of the heart providing access into a ventricle of the heart, and specifically the left ventricle. In one example, illustrated in FIG. 3A, the tissue to be cored 91 may be a heart wall 90 that is within the perimeter of a sewing ring 80.

In this embodiment, and prior to use of the coring tool 10, the sewing ring 80 is attached by known means to the heart wall tissue 90 in a position where the implantation of the VAD is desired. Once the sewing ring is secured the operator can create an incision, such as cross-slits 92 in the tissue to be cored 91. The cross-slits will assist with passage of the core tool 10 as they create multiple flaps of tissue which may part from one another upon passage of the coring tool 10.

Figure 3B:
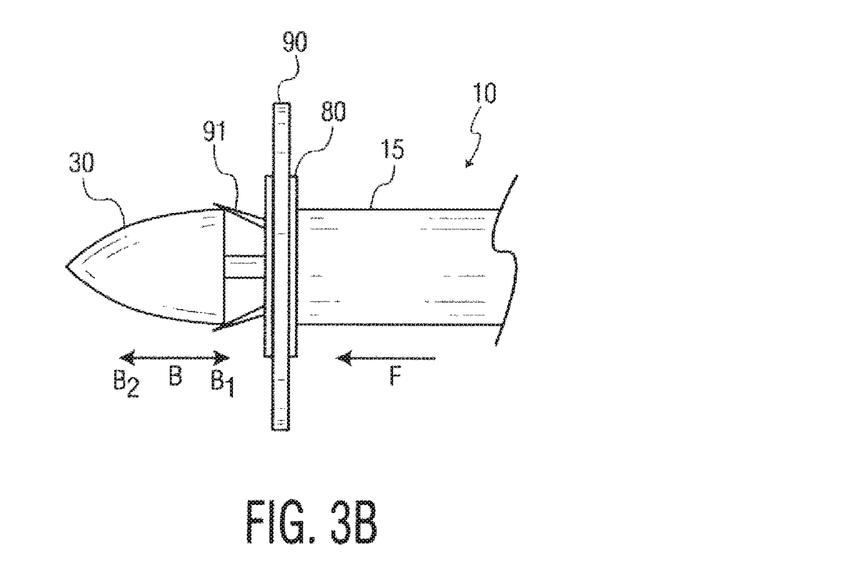
FIG. 3B illustrates how, in one instance, the coring tool of FIG. 1 can be positioned relative to the sewing ring and heart wall of FIG. 3A.

As illustrated in FIG. 3B, the distal coring head 30 is directed to the tissue 91. Preferably, the diameter of the proximal-most portion of the coring head and the shaft 15 of tool 10 is nearly the same size as the inner diameter of the sewing ring 80 such that, upon coring, most of the tissue 91, nearly all of the tissue 91, or, preferably, substantially all of the tissue 91 within the perimeter of the sewing ring is removed. The coring head may then be passed through the tissue 90 such that the distal-most portion of the shaft is adjacent to the sewing ring. Specifically, the tool 10 should be positioned such that the interface between the coring head and the shaft should be on the same plane as the tissue 91 to be cored such that the blade 35 of the coring head will likewise meet the distal end of the shaft at that plane to perform the coring action.

With the tool 10 so positioned, the operator can apply the force to the operator interface element 25, such as a squeezing motion (if the element 25 is a trigger) or the like, to move the coring head 30 from the first position $B_1$ to the second position $B_2$. FIG. 3B illustrates the tool relative to the sewing ring 80 and tissue 91 as the coring head approaches the second position, where the coring head advances into and past the tissue 91. Once in the second position, the tissue 91 may return to its original position, though the actuation rod 31 is now positioned through the cross-slit 92. Also once the coring head reaches the second position, the force may be removed from the operator interface element, though the coring head will remain in the second position. The operator may at this point toggle the selector mechanism and, upon applying the force to the operator interface element a second time, the coring head may return to the first position. As the coring head moves to the first position, the coring head can trap the tissue 91 in between the distal end of the shaft 15 and the blade 35 of the coring head. Upon the coring head attaining the first position, the blade 35 can sever or core the tissue 91, which becomes trapped within the hollow volume of the coring head, which is now a closed volume against the distal end of the shaft. The tool 10 may be removed from the patient, along with the cored tissue still trapped within the volume of the coring head.

As such, the coring tool 10 provides for a simplified, repetitive motion for actuating the distal coring head 30 between the first and second positions. The coring tool 10 allows for a single-handed operation by the operator, which can be particularly useful during a surgical procedure. Furthermore, the shaft 15 of the tool 10 provides a distance between the coring head and the operator interface element such that the hand or hands of the operator remain outside of the patient.

Furthermore, the design of the handle provides another important advantage in that it allows the operator to maintain forward, or distal, pressure on the coring tool 10 throughout the entire surgical procedure. During this surgical procedure, it is important to minimize blood flow out of the tissue 91, and thus, throughout the process, care should be taken to maintain the coring tool against the sewing ring 80 to minimize blood loss. As a further example, the design of the shaft 15 may include a blunt, closed distal portion adapted to form a partial or complete seal with the sewing ring. Further, the shaft may be equipped with seals around the actuation rod 31 such that, while the distal coring head is in the second position, spaced from the shaft, blood cannot freely flow out of the sewing ring into the shaft. The design of the operator interface element, and the handle grip 22, may allow the operator to direct consistent forward pressure on the sewing ring. For example, even when pulling on the trigger-type interface element (as illustrated), the operator can still maintain forward force using the rest of her hand positioned against the handle grip 22.

It is envisioned that alternative methods of use and surgery can be performed with the coring tool 10 of the present invention, and similarly, that adjustments or changes may be made to the tool to accommodate different surgical procedures, such as a longer shaft, different style of handle, larger or smaller dimensions, and the like.

For example, in one variation, rather than or in addition to the pulleys 47a, 47b, 47c having a ratchet clutch mechanism, the interdigitating teeth 46a, 46b, 41, 42 may be tapered in one direction, such that upon application of the force on the operator interface element 25, the teeth interact to actuate the actuator rod 31 and coring head 30, but upon release of the force, and movement in the opposite direction by the operator interface element and the selected actuator 45a or 45b, the tapered surfaces of the teeth merely slide such that the reverse movement of the selected actuator does not result in corresponding reverse movement by the actuator rod. Other such designs are also envisioned.

Additionally, while the primary embodiment of the coring tool 10 is described herein as to the structure and use of the tool, it is envisioned that alternative structures may also be used which are within the parameters of the present invention. For example, the operator interface element 25 may be something other than a trigger, such as a push-button, wheel, knob, or the like. Similarly, the grip of the handle may have another form other than a pistol-type grip. Likewise, the actuation mechanism may include mechanics and/or linkages other than the rack-and-pinion actuators and pulley system. For example, the rack-and-pinion design could be replaced with a length of threading on the actuation rod and two, opposing threaded actuators selectably engageable thereto. Still another alternative could include a multi-gear system directly connecting the operator interface element to the actuation rod.

Furthermore, the distal coring head could also vary according to design or intent of use. For example, the coring head could be rotatable, in addition to movable along direction B. The rotating action could allow for improved cutting or coring capability. The rotation could be actuated through the actuator rod, such as by a secondary knob or the like positioned on the handle, or by any other mechanism.

Figure 4A:
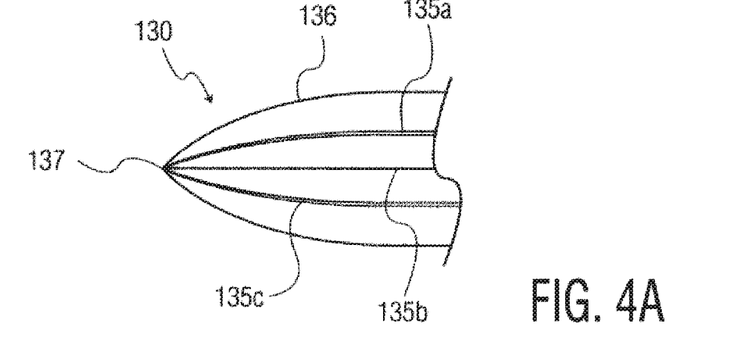
Figure 4B:
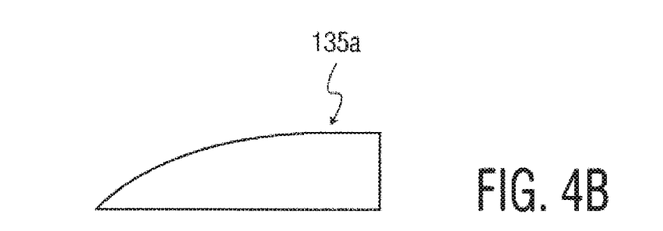

In yet another alternative, illustrated in FIGS. 4A and 4B, the coring head 130 itself could have an alternative design, such as having multiple blades 135a, 135b, 135c thereon rather than just the single blade as illustrated in FIG. 1A. For example, the coring head could have a collet design, where the coring head, in the second, open position, exposes a plurality of blades 135a, 135b, 135c positioned in a longitudinal direction (i.e., in a proximal-distal direction). The plurality of blades, each have a shape similar to blade 135a illustrated in FIG. 4B, is positioned within the coring head 130, which has a similar shape as coring head 30 as including a tapering outer surface 136 to a distal-most tip 137. Other such design variations are also envisioned.

Figure 5:
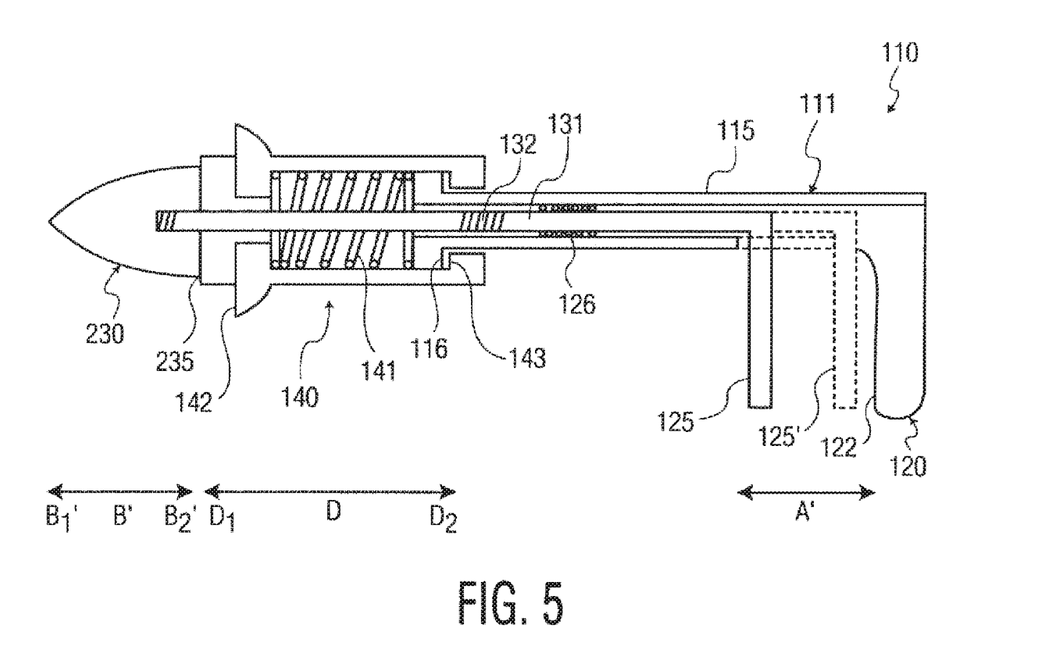
FIG. 5 illustrates another embodiment of a coring tool of the present invention.

In still another alternative embodiment, FIG. 5 illustrates a coring tool 110 of the present invention including a frame 111 incorporating a handle 120 and a hollow shaft 115 extending in the distal direction from the handle. A distal coring head 230 is disposed distal to shaft 115. The coring head 230 is similar in structure to coring head 30 (or alternatively, coring head 130) and includes at least one blade 235 on a proximal surface of the coring head 230.

The coring head 230 is actuatable, via an actuation rod 131 extending through the shaft 115, in the direction "B'" between a distal, first position $B_1'$, and a proximal, second position $B_2'$. In this embodiment, the rest position of the coring head 130 is the first position $B_1'$, while the actuated position is the second position $B_2'$.

Opposite the distal coring head 230, and integrated with shaft 115, is the handle 120. The handle includes a handle grip 122 which can be ergonomically shaped for steady and comfortable gripping by a hand of the operator. An operator interface element 125, such as a trigger (as illustrated) or the like, is positioned relative to the frame 111 adjacent handle 120. The operator interface element 125 is movable in a direction relative to the frame between a rest position illustrated in solid lines in FIG. 5, and an actuated position depicted in broken lines (as handle 125'). In the depicted embodiment of FIG. 5, the operator interface element 125 is mounted for translating motion relative to the frame 111 as indicated by arrow "A'" between the rest position and the actuated position. In the rest position, the operator interface element 125 is remote from the handle 120, whereas in the actuated position the operator interface element 125 is adjacent handle 120. As illustrated, for example, the operator interface element 125 is biased toward the rest position by a first biasing mechanism 126, such as spring 126, positioned relative actuation rod 131, which may also bias the coring head 230 towards a rest position at the distal, first position $B_1'$, via actuation rod 131. For example, the spring 126 may be affixed at one end to the shaft 115 and at the other end to the actuation rod 131 to create the bias force for both the interface element 125 and the coring head 230.

The coring tool 110 also includes an actuation mechanism 140 mounted to frame 111 towards a distal end of the shaft 115. The actuation mechanism 140 includes an abutment 142 and a second biasing mechanism 141, such as spring 141, for translating motion of the actuation mechanism 140 relative to the frame 111 and shaft 115 along arrow "D" between a rest position, indicated as distal, first position $D_1$, and an actuated position, indicated as proximal, second position $D_2$. The rest position ($D_1$) can be maintained by counterbalancing the force of the spring 141 with cooperating shoulders 116, 143 such that, upon contacting one another, the shoulders inhibit further distal movement of the actuation mechanism 140. In the rest position, the blade 235 of the coring head 230 can contact a distal surface of the actuation mechanism 140 to create a hollow, substantially closed volume within coring head 230.

Continuing with this exemplary alternative embodiment, an example of a method of operation of this coring tool 110 is described. As illustrated in FIG. 5, the actuation of the coring head 230 and actuation mechanism 140 can result in relative movement between the coring head and actuation mechanism. For example, applying a force to the abutment 142 may force the actuation mechanism 140 in the proximal direction, towards position $D_2$. Once in this proximal position, the coring head 230 would now be spaced apart from the actuation mechanism 140. With the actuation mechanism positioned in this proximal direction, the operator interface element 125 can then be moved to the actuated position 125', thereby moving the actuation rod 131, and thus, the coring head 230, proximally until coring head 230 reaches the second, proximal position $B_2'$, at which point the blade 235 is again in contact with the distal surface of the actuation mechanism 140. With the operator interface element 125 actuated, the actuation mechanism 140 may remain in this proximal position (at $D_2$), even once the force against the abutment 142 is removed. Then, once the operator interface element 125 is returned to the rest position, both the coring head 230 and actuation mechanism 140 can return to their respective rest positions $B_1'$, $D_1$.

In one variation, the actuation rod 131 can include a rotational element 132 such that, upon actuation of the operator interface element 125, the actuation rod 131 rotates which results in rotation of the coring head 230. For example, the rotational element 132 may be a spiral or corkscrew shape along a portion of the length of the actuation rod. The shaft 115 may also include a matching shape along a portion of the length (not shown), such that the matching shapes interact, upon actuation, causing the actuation rod to rotate. The actuation rod 131, in this instance would also require a rotating connection (not shown) positioned along its length between the rotational element 132 and the operator interface element 125 so that the element 125 does not rotate along with the coring head 230 and portion of the actuation rod 131. Such a connection may be any as known in the art, such as matching, coaxial, cylindrical shapes held together by threading, matching shoulders (to prevent separation), or the like. Such rotation can be useful in providing a shearing motion of the blade 235 against tissue during a coring operation which may assist in improved coring. However, the leverage attained by the operator using the handle 120 and interface element 125 may provide sufficient force to core the tissue, though such rotation may still be included.

This alternative embodiment may also be used, as coring tool 10 above, in a method of forming a core or cut in tissue, such as heart wall tissue. Reference will be made to FIGS. 3A and 38 as the coring head 230 can operate in a similar manner.

In this embodiment, the sewing ring 80 is attached and an incision, such as cross-slits 92, is formed in the tissue to be cored 91 as discussed above. Similar to that illustrated in FIG. 3B, the distal coring head 230 is directed to and through tissue 91 until the abutment 142 contacts the sewing ring (or surrounding tissue, if no sewing ring is present). With the abutment so positioned, a force is applied on the handle 20 by the operator which creates an opposite force applied by the sewing ring on the abutment which causes the abutment, and actuation mechanism 140 as a whole, to move in a proximal direction to position $D_2$ while compressing spring 141. In effect, the actuation mechanism 140 remains largely stationary against the sewing ring while the handle, shaft 115, actuation rod 131 and coring head 230 all move distally relative to the actuation mechanism 140, sewing ring and tissue 91 until the coring head 230 advances past tissue 91 and is positioned within the heart. In this position, the coring head has remained in the rest position $B_1'$.

While maintaining the force on the sewing ring, the operator can now actuate the operator interface element 125 to the actuated position which moves distal coring head 230 to the second, proximal position $B_2'$ and once again the blade 235 is positioned against the distal surface of the actuation mechanism 140, having created the core in tissue 91. If the tool 110 includes the rotational element 132, the coring head 230 may rotate as it travels towards the second, proximal position which may increase shearing forces applied to the tissue which can improve the coring process. The cored tissue remains inside coring head 230, as discussed above.

Having completed the tissue coring, the operator can now, maintaining the operator interface element 125 in the actuated position, retract the tool 110 from the heart, sewing ring and patient while keeping the cored tissue within the volume of the coring head 230.

Similar to coring tool 10, coring tool 110 allows the operator to maintain forward, or distal, pressure on the coring tool, and thus the sewing ring, throughout the entire surgical procedure, as discussed above. Furthermore, this variation of coring tool 110 can result in an even further simplified surgical procedure as the operator need only actuate the operator interface 125 once to perform the coring operation since the coring head 230 extends distally merely by actuating the actuation mechanism 140 through a distally-directed force, applied on the handle 120, rather than having to actuate the interface element twice (as is required using tool 10).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of coring a tissue comprising:
   (a) positioning a coring tool adjacent the tissue;
   (b) manually moving an operator interface element of the coring tool relative to a frame of the coring tool from a rest position toward an actuated position so as to advance a coring head in a distal direction relative to the frame causing the coring head to advance into the tissue;
   (c) returning the operator interface element toward the rest position while leaving the coring head in position relative to the frame;
   (d) manually moving the operator interface element of the coring tool toward the actuated position again so as to retract the coring head in a proximal direction relative the frame and thus retract the coring head relative to the tissue; and
   (e) moving an actuator selector element of an actuation mechanism from a first position to a second position between steps (b) and (d) and when the actuator selector is in the first position the coring head moves distally responsive to movement of the operator interface element from the rest position toward the actuated position and when the actuator selector is in the second portion the coring head moves proximally responsive to movement of the operator interface element from the same rest position toward the same actuated position, the actuator selector element being configured to engage a pair of actuators within the coring tool, the pair of actuators defining a rack and pinion system.

2. A method as claimed in claim 1 wherein the steps of moving the operator interface element toward the actuated position include squeezing the operator interface element toward a handle incorporated in the frame.

3. A method as claimed in claim 2 wherein the manually moving steps are performed using one hand, and wherein the same hand is used to grasp the handle and maintain the frame of the coring tool in position relative to the tissue.

4. A method as claimed in claim 3 wherein the step of maintaining the frame in position relative to the tissue includes maintaining the frame in engagement with a sewing ring attached to the tissue.

5. A method as claimed in claim 4 wherein the tissue is a wall of a heart in a mammalian subject.

6. A method as claimed in claim 1 wherein the coring head has a blade facing in the proximal direction so that the coring head cuts a core from the tissue during step (d).

* * * * *